United States Patent [19]

Hetzel et al.

[11] Patent Number: 4,760,317
[45] Date of Patent: Jul. 26, 1988

[54] ELECTRICAL ARRANGEMENT FOR DRIVING A ROTARY TOOL FITTED IN A HANDPIECE

[75] Inventors: Max Hetzel, Deitingen; Vincent Mosimann, Bienne, both of Switzerland

[73] Assignee: Bien-Air SA, Switzerland

[21] Appl. No.: 76,387

[22] Filed: Jul. 22, 1987

[30] Foreign Application Priority Data

Jul. 23, 1986 [CH] Switzerland ..................... 2944/86

[51] Int. Cl.⁴ ............................................. H02P 6/02
[52] U.S. Cl. .................................................. 318/254
[58] Field of Search ............... 318/254, 138, 255, 256, 318/280, 333, 410, 411, 439, 440, 441, 442, 479, 504, 558

[56] References Cited

U.S. PATENT DOCUMENTS

| | | | |
|---|---|---|---|
| 3,930,186 | 12/1975 | Sekiya et al. ................ | 318/471 X |
| 4,004,202 | 1/1977 | Davis ........................... | 318/138 |
| 4,338,556 | 7/1982 | Hetzel .......................... | 318/434 X |
| 4,341,982 | 7/1982 | Lahti et al. .................. | 318/51 |
| 4,617,499 | 10/1986 | Yuasa .......................... | 318/254 |

FOREIGN PATENT DOCUMENTS

| | | |
|---|---|---|
| 0065927 | 12/1982 | European Pat. Off. . |
| 0088626 | 9/1983 | European Pat. Off. . |
| 2801520 | 7/1979 | Fed. Rep. of Germany . |
| 57-22396 | 2/1982 | Japan ................................. 318/254 |
| 2039095 | 7/1980 | United Kingdom ............... 318/254 |

*Primary Examiner*—Bentsu Ro
*Attorney, Agent, or Firm*—McGlew and Tuttle

[57] ABSTRACT

The arrangement comprises an external supply unit that feeds into two flexible conductors (5, 5') a variable d.c. voltage ($V_A$) superposed on a modulated high frequency voltage ($V_C$), the modulation being dependent on the position of a switch. The arrangement further comprises, inside a handpiece, means (20, 21) connected to the conductors for receiving therefrom and separating the two voltages, means (23, 25, 26, 27, 28, 29) for feeding a supply voltage ($V_D$) to the circuits of the handpiece, means (30, 31, 33, 34) for demodulating the high frequency voltage and for generating a logic signal ($S_L$) representative of the position of the switch, a three-phase motor, sensors (A, A', A'') controlled by the motor, an inverting circuit (41) receiving the logic signal, a control circuit (50), and a drive circuit (60) issuing a three-phase signal ($S_M$, $S'_M$, $S''_M$) to the terminals (X, X', X'') of the motor.

The speed of the motor is determined by the d.c. voltage being applied and the direction of rotation is determined by the position of the switch.

12 Claims, 2 Drawing Sheets

ELECTRICAL ARRANGEMENT FOR DRIVING A ROTARY TOOL FITTED IN A HANDPIECE

BACKGROUND OF THE INVENTION

1. Field of the Invention

This invention relates to an electrical arrangement for driving at high speed a rotary tool, e.g. a bit in a surgeon's or dentist's handpiece such as a bur or drill. It is concerned more particularly with a driving arrangement involving an electric motor having a rotor.

2. Prior Art

Known arrangements of this kind comprise an external supply unit and a collector motor mounted in the handpiece, the supply and the motor being connected by a flexible lead having two conductors. The supply unit provides a voltage that can be adjusted, e.g. by means of a pedal, and enables the user of the handpiece to change at will the speed of rotation of the motor and hence of the tool driven by it.

However, the use of a d.c. or a.c. motor having brushes in a dental handpiece has a number of drawbacks.

Firstly, because of the motor's high speed of rotation, at times over 100,000 revolutions per minute, the wear on the brushes is considerable. Secondly, because the motor operates in a moist environment that contains in suspension particles of drilling residue, it is impossible to avoid, despite the sealing means that are provided, deterioration of the brushes and associated parts due to condensation and due to the accumulation of dirt on their surfaces. Thirdly, if the operator uses volatile products, the sparks that are generated by the brushes may cause local explosions.

Brushless d.c. motors that do not suffer from these drawbacks are also known. They are motors having a stator usually with three delta- or star-connected windings, and a magnetized rotor. The windings are energized by an electronic circuit that is controlled by the position of the rotor by means of three stationary sensors on the motor. A motor of this kind for industrial use is for instance described in U.S. Pat. No. 4,338,556.

The presence of three stator windings and of three sensors naturally causes the electrical connections to be more complicated. A motor of this kind requires at least eight connection wires, i.e. three wires for the windings, three wires for the sensors and two wires for the sensors' supply. These eight wires form a flex that is more cumbersome, more rigid and less reliable than a two-wire flex.

This drawback is particularly bothersome in the case of a dentist's drill as the movements of such a drill should only be hampered in the least possible way.

SUMMARY OF THE INVENTION

An object of the invention is to overcome this drawback by providing an electrical driving arrangement for a drill or other handpiece in which the electrical connection with the handpiece may consist of a two-wire flex.

The electrical driving arrangement provided by the invention comprises, external to the handpiece:

electrical supply means having an output, a source of d.c. voltage, a generator for supplying a high frequency voltage and means for superposing said high frequency voltage on said d.c. voltage and applying the resulting compound voltage to said output;

two deformable electric conductors, having one end thereof connected to said output; and further comprises in said handpiece:

a multi-phase, brushless motor having a magnetized rotor arranged to rotate said tool;

means connected to the other end of said two conductors to receive said compound voltage and adapted to separate therefrom said d.c. voltage and said high frequency voltage;

sensor means controlled by said rotor and adapted to generate, during operation, logic signals that are representative of the rotor's angular positions;

a logic control circuit arranged to generate control signals in response to logic signals generated by the sensor means;

a drive circuit connected to the motor and arranged to receive said control signals and said d.c. voltage and to issue a multi-phase signal to the motor to cause its rotor to rotate; and a rectifying circuit arranged to receive said high frequency voltage and to issue a d.c. voltage to the sensor means, to the control logic circuit and to the drive circuit.

Besides the flexibility and reliability of the electric link between the supply means and the handpiece in the above arrangement, a further advantage is that this link remains compatible with a handpiece fitted with a motor having brushes. In such a case one need only stop the high frequency voltage so as only to supply d.c. voltage to the motor.

BRIEF DESCRIPTION OF THE DRAWINGS

In the accompanying drawings, given by way of example and in which the same references have been used for corresponding parts.

DETAILED DESCRIPTION

Figure 1:
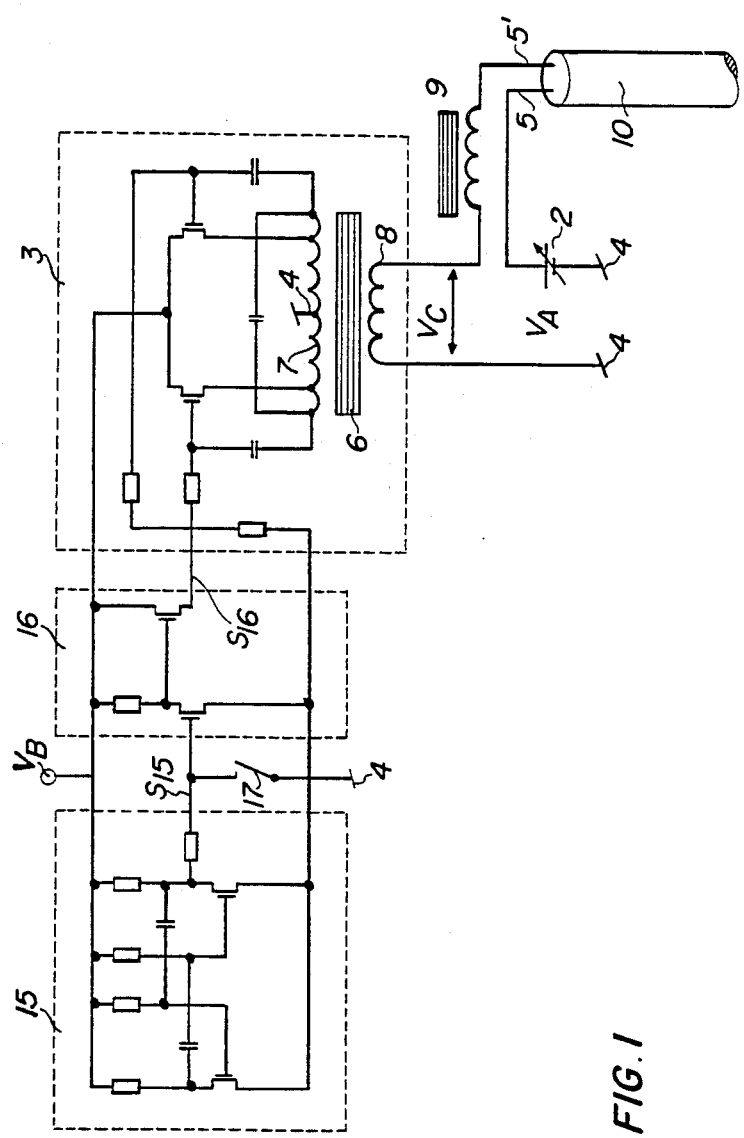
FIG. 1 is a diagram of one form of supply means that may be used in an arrangement according to the invention.

The supply means of FIG. 1 are made up mainly of a d.c. voltage source 2 and of a high frequency generator 3. Source 2 is connected to the mains and generates a d.c. voltage $V_A$. Preferably a control unit, not shown, e.g. a pedal, is provided to vary voltage $V_A$ between, say, 0 and 24 volts. One pole of source 2, e.g. the negative pole, is connected to a ground terminal 4 and the other pole is connected to one end of a flexible electric conductor 5.

Generator 3 comprises a transformer 6 having a primary winding 7 and a secondary winding 8. Winding 7 is connected to an electronic oscillator circuit of known type and which therefore will not be described here. A source not shown issues a supply voltage $V_B$ to the oscillator circuit which generates across secondary winding 8 an a.c. voltage $V_C$ having a frequency of 2 MHz and an amplitude of about 1 volt. One end of secondary winding 8 is connected to ground terminal 4, while its other end is connected to one end of a second flexible electric conductor 5' via a self-inductance coil 9. Conductors 5 and 5' are joined in a flex or lead 10 leaving the supply means. Coil 9 plays no major part in the illustrated arrangement. Its function will be explained later and may be ignored in the meantime.

The supply means further comprise a low frequency oscillator 15 and a modulating circuit 16, both circuits being supplied by the source providing voltage $V_B$. The oscillator may for instance be an asymmetric flip-flop of known kind which will therefore not be described here and which issues a low frequency periodic signal $S_{15}$ made up of short positive pulses, the length of each pulse being equal to 10% of the period of the signal. Circuit 16 is basically a non-linear amplifier of known kind made up for instance of two transistors connected in cascade. Circuit 16 receives signal $S_{15}$ and issues to generator 3 a signal $S_{16}$ having sufficient energy to modulate, by a method that is also known, the amplitude of the frequency voltage by the low frequency signal. The modulation is done in such a way that the high frequency oscillation stops during the pulses of signal $S_{15}$, the high frequency voltage thus having the shape of an oscillation that is periodically interrupted for brief moments.

Between the output of oscillator 15 and ground 4 an on-off switch 17 is also provided. When open, switch 17 is of no effect, whereas when closed, the output of oscillator 15 is grounded. Thus in one position of switch 17 the amplitude of the high frequency voltage is modulated by the low frequency signal, and in the other position of switch 17 the modulation is stopped, which may also be considered as a modulation of zero amplitude. Therefore, each position of switch 17 produces a particular modulation mode.

Instead of having its amplitude modulated by the means just described, the high frequency voltage could of course be modulated in a different way, e.g. by frequency modulation, so long as one position of switch 17 corresponds to one mode of modulation and the other position of switch 17 corresponds to another mode of modulation.

Figure 2:
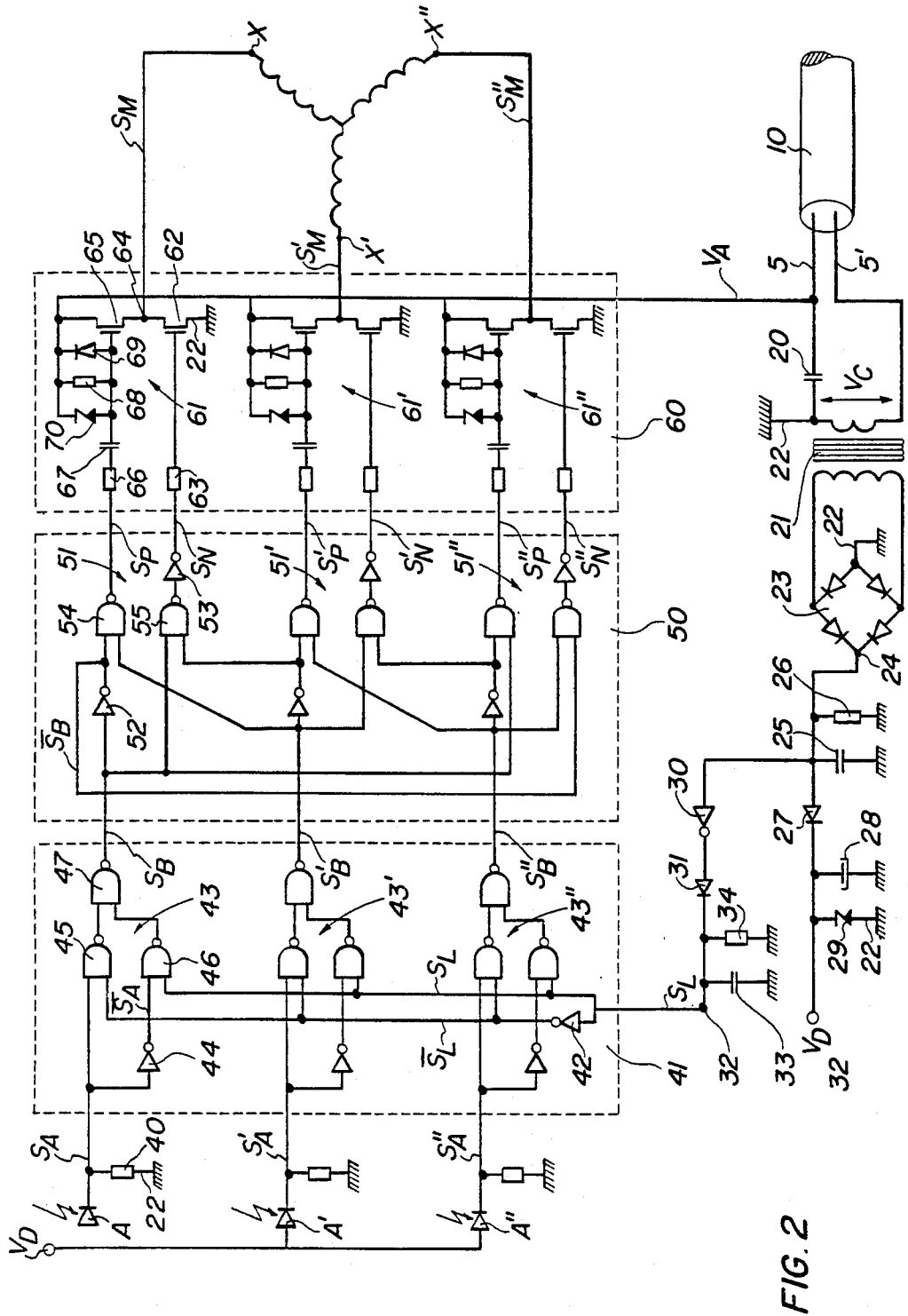
FIG. 2 is a diagram of some circuits associated with an electric motor, these circuits and the motor forming another part of the above arrangement according to the invention and which are housed in a handpiece.

The voltage between conductors 5 and 5' is equal to the superposition, or the sum of voltages $V_A$ and $V_C$. This compound voltage is transmitted via flex 10 to the handpiece circuits shown in FIG. 2.

At the handpiece end, conductor 5 is connected to one terminal of a decoupling capacitor 20, and conductor 5' is connected to one end of the primary winding of a voltage step-up transformer 21. The other end of this primary winding along with the other terminal of capacitor 20 are connected to a ground terminal 22 of the handpiece. In this way d.c. voltage $V_A$ and high frequency voltage $V_C$ are separated with voltage $V_A$ being applied across capacitor 20 and high frequency voltage $V_C$ being applied across the secondary winding of transformer 21. Ground terminals 4 and 22 are connected galvanically and have virtually the same d.c. and a.c. potential.

The secondary winding of transformer 21 is connected to the input terminals of a bridge rectifier 23. One output terminal of bridge 23 is connected to ground terminal 22. Between the other output terminal 24 and ground, a rectified high frequency voltage then appears having an amplitude of about 10 $V_C$, i.e. typically 15 volts from peak to peak. When switch 17 is open, this voltage of course disappears during the pulses of low frequency signal $S_{15}$.

A filter, made up of a capacitor 25 and of a resistor 26 connected in parallel between ground 22 and terminal 24, removes the high frequency component of the signal issued by bridge rectifier 23. Depending on whether switch 17 is closed or open, the voltage on terminal 24 is thus either d.c., or complementary to low frequency signal $S_{15}$.

A rectifier 27, connected to terminal 24, generates a d.c. supply voltage $V_D$ for the electronic circuits in the handpiece, the voltage being filtered by a capacitor 28 and stabilized by a Zener diode 29. The input of an inverter 30 is also connected to terminal 24, its output issuing either a zero voltage, when switch 17 is closed, or a voltage having a shape identical to that of signal $S_{15}$, when switch 17 is open. Additionally, one terminal of a rectifier 31 is connected to the output of inverter 30 to issue to the other terminal 32, to which is connected a filter made up of a filtering capacitor 33 and a resistor 34 connected in parallel between this terminal and ground terminal 22, a logic signal $S_L$. This signal is low, i.e. at logic level "0", when switch 17 is closed, and high, i.e. at logic level "1", when switch 17 is open.

In the handpiece is mounted a three-phase motor, not shown, having a stator whose windings are star-connected between output terminals X, X' and X". The motor's rotor comprises a permanent magnet whose poles are opposed diametrically with respect to the axis of rotation of the rotor. By applying suitable signals to terminals X, X' and X", a rotating magnetic field can be generated in the stator thereby to produce synchronized rotation of the rotor.

The purpose of the electronic circuitry that is fitted in the handpiece and which will be described below, is to generate these signals. A motor having delta-connected windings or operating with a number of phases other than three, could also be used. This would involve making a few minor changes to the electronic circuitry, known to the man of the art.

Three sensors A, A' and A" are fitted in the handpiece around a circle centered on the axis of rotation of the motor's rotor. The sensors are stationary with respect to the motor's stator and are spaced from one another by 120° around the circle. The sensors are preferably of a photoelectric type, e.g. phototransistors. In this case a permanent light source, not shown, is associated with each sensor in order to light it up. Other sensors, such as Hall effect cells, could also be used. One terminal of sensor A is connected to the supply providing voltage $V_D$. The other terminal of sensor A is connected to ground terminal 22 via a load resistor 40, to whose terminals a logic signal $S_A$ is applied, generated for instance by an interface circuit not shown. Signal $S_A$ is low when sensor A is not activated, and high when sensor A is activated. Sensors A' and A" are connected in the same way as sensor A and generate respectively logic signals $S'_A$ and $S''_A$.

The sensors, assuming they are phototransistors, are controlled by a semicircular opaque disc that is fixed to the rotor between the sensors and the light sources. Under these conditions, depending on the angular position of the disc, there will always be one lighted, i.e. activated, sensor and two obstructed sensors, or conversely. The state of the sensors defines six consecutive angular zones, $Z_1, Z_2 \ldots Z_6$, which enable the position of the rotor to be determined with an accuracy of 60°. Each zone $Z_i$ (i=1 to 6) is thus defined by the logic states of signals $S_A$, $S'_A$ and $S''_A$, which will be referenced $Z_i (S_A, S'_A, S''_A)$. Thus, in a given direction of rotation, the zones will for instance succeed one another in the following order: $Z_1$ (100), $Z_2$ (110), $Z_3$ (010), $Z_4$ (011), $Z_5$ (001), $Z_6$ (101). In the opposite direction of rotation the order of succession of the zones will of course be reversed.

Signals $S_A$, $S'_A$ and $S''_A$ are applied to a logic inverting circuit 41 which further receives signal $S_L$. Circuit 41 comprises an inverter 42 to whose input signal $S_L$ is applied, and three identical cells 43, 43' and 43", respectively receiving signals $S_A$, $S'_A$ and $S''_A$. Only cell 43 will be described here. It comprises an inverter 44 and three two-input NAND gates 45, 46 and 47. Signal $S_A$ is applied to the input of inverter 44 and to one input of gate 45 whose output is connected to one input of gate 47. The output of inverter 44, which issues a signal $\bar{S}_A$ opposite to signal $S_A$, is connected to one input of gate 46 whose output is connected to the second input of gate 47. The second input of gate 46 receives signal $S_L$ while the second input of gate 45 is connected to the output of inverter 42 in order to receive signal $\bar{S}_L$, opposite to signal $S_L$. The output of gate 47 issues a signal $S_B$, and the outputs of cells 43' and 43" issue respectively a signal $S'_B$ and a signal $S''_B$.

When signal $S_L$ is low, the output of gate 46 goes high, whatever the logic level at the output of inverter 44. The output of inverter 42 being high, gate 45 issues on its output a signal $\bar{S}_A$, opposite to signal $S_A$, and gate 47 issues on its output a signal opposite to $\bar{S}_A$, i.e. it restores signal $S_A$. Thus $S_B = S_A$ if $S_L = 0$. In this case, circuit 41 causes no change in signal $S_A$.

But a high logic level of signal $S_L$ generates on the output of gate 47 a signal opposite to signal $S_A$. Therefore $S_B = \bar{S}_A$ if $S_L = 1$.

The same applies of course to cells 43' and 43". Circuit 41 thus generates on its output signals that are identical to the signals of sensors A, A', A" when $S_L = 0$, and opposite signals when $S_L = 1$.

Signals $S_B$, $S'_B$ and $S''_B$ are then applied to a logic control circuit 50. This circuit comprises three identical cells 51, 51' and 51". Only cell 51 will be described here. It comprises two inverters 52 and 53 and two two-input NAND gates 54 and 55. Signal $S_B$ is applied to the input of inverter 52 and to one input of gate 55. One input of gate 54 is connected to the output of inverter 52 while its other input receives signal $S'_B$. The other input of gate 55 receives a signal $\bar{S}_B$ opposite to signal $S_B$, issued by the output of an inverter 52' of cell 51', equivalent to the inverter 52 of cell 51. The output of gate 54 issues a logic signal $S_P$ while the output of gate 55 is connected to the input of inverter 53 which issues on its output a logic signal $S_N$.

Similarly, cell 51' receives signals $S'_B$, $S''_B$ and $\bar{S}''_B$ to issue signals $S'_P$ and $S'_N$, and cell 51" receives signals $S''_B$, $S_B$ and $\bar{S}_B$ to issue signals $S''_P$ and $S''_N$.

The output signals of control circuit 50 are then applied to the input of a drive circuit 60. This circuit comprises three identical cells, 61, 61' and 61", the first only being described. Cell 61 comprises an N-type MOS power transistor 62 whose source is connected to ground terminal 22 and whose gate is connected to the output of inverter 53 via a protective resistor 63 to receive $S_N$. The drain of transistor 62 is connected at a point 64 to the drain of a P-type MOS power transistor 65 whose source receives supply voltage $V_A$ and whose gate receives signal $S_P$ via a protective resistor 66 and a coupling capacitor 67. The gate and the source of transistor 65 are also connected to each other, first, via a resistor 68 which defines the working point of the transistor and, second, via a diode 69 and a Zener diode 70 which limit the amplitude of the signal to the gate.

In response to signals $S_N$ and $S_P$, which may possibly be adapted to circuit 60 by means of an interface circuit not shown, cell 61 issues to point 64 a drive signal $S_M$ which is applied to terminal X of the stator windings. Similarly cells 61' and 61" issue respectively signals $S'_M$ and $S''_M$, the first being applied to terminal X' and the second to terminal X".

Depending on the levels of signals $S_N$ and $S_P$, point 64 of cell 61 may be in any one of three different states. If $S_N = S_P = 0$, transistor 62 is blocked and transistor 65 is saturated. The voltage at point 64 is then equal to $V_A$. Thus, in this case, $S_M = V_A$. If $S_N = S_P = 1$, transistor 62 is saturated and transistor 65 is blocked. In such a case the voltage at point 64 is zero and $S_M = 0$. And if $S_N = 0$ and $S_P = 1$, both transistors are blocked. The impedance considered from point 64 is then finite and the voltage at point 64 is indeterminate, which is noted as $V_M = ?$. In this case no current can flow between point 64 and terminal X. There remains the possibility $S_N = 1$ and $S_P = 0$, producing a simultaneous saturation of both transistors and a shortcircuiting of the supply generating voltage $V_A$. This corresponds to a prohibited state which cannot occur, with the circuits described, in any of the angular zones $Z_i$ ($i = 1$ to 6). The above about cell 61 applies of course also to cells 61' and 61" which generate respectively signals $S'_M$ and $S''_M$.

To each angular zone $Z_i$ correspond well defined states for the output signals of circuits 41, 50 and 60 described above. The table below shows the state of these signals, in the case where $S_L = 0$, in dependence on the states of signals $S_A$, $S'_A$ and $S''_A$.

| $S_L = 0$ | $S_A$ | $S'_A$ | $S''_A$ | $S_B$ | $S'_B$ | $S''_B$ | $S_N$ | $S_P$ | $S'_N$ | $S'_P$ | $S''_N$ | $S''_P$ | $S_M$ | $S'_M$ | $S''_M$ |
|---|---|---|---|---|---|---|---|---|---|---|---|---|---|---|---|
| $Z_1$ | 1 | 0 | 0 | 1 | 0 | 0 | 1 | 1 | 0 | 1 | 0 | 0 | 0 | ? | $V_A$ |
| $Z_2$ | 1 | 1 | 0 | 1 | 1 | 0 | 0 | 1 | 1 | 1 | 0 | 0 | ? | 0 | $V_A$ |
| $Z_3$ | 0 | 1 | 0 | 0 | 1 | 0 | 0 | 0 | 1 | 1 | 0 | 1 | $V_A$ | 0 | ? |
| $Z_4$ | 0 | 1 | 1 | 0 | 1 | 1 | 0 | 0 | 0 | 1 | 1 | 1 | $V_A$ | ? | 0 |
| $Z_5$ | 0 | 0 | 1 | 0 | 0 | 1 | 0 | 1 | 0 | 0 | 1 | 1 | ? | $V_A$ | 0 |
| $Z_6$ | 1 | 0 | 1 | 1 | 0 | 1 | 1 | 1 | 0 | 0 | 0 | 1 | 0 | $V_A$ | ? |

To one given angular zone $Z_i$ corresponds only one current in the motor windings, this current flowing from the terminal at voltage $V_A$ to the terminal having a zero voltage. This current generates within the stator a radial magnetic field. On moving from one zone $Z_i$ to the next, the magnetic field rotates through 60°.

Signals $S_M$, $S'_M$, $S''_M$ thus form together a three-phase signal generating in the motor's stator a rotating magnetic field. The direction of rotation of the field depends on the order of succession of angular zones $Z_i$. This order, and hence the direction of rotation of the motor, is determined by the direction of the torque that is applied by the rotating magnetic field on the rotor.

In the case $S_L = 1$, signals $S_B$, $S'_B$, $S''_B$ are opposite signals to signals $S_A$, $S'_A$, $S''_A$, respectively. This causes, in each line of the above table a reversal of signals $S_N$ . . . $S''_P$ and a permutation between the values 0 and $V_A$ of signals $S_M$, $S'_M$, $S''_M$. It follows therefore, in this case, that for each angular zone $Z_i$, the current in the windings flows flows in a direction which is opposite to that of the current which flows when $S_L = 0$. Thus, the direction of the rotating magnetic field and the direction of the torque it applies to the rotor are also opposite in both cases. It follows therefore that, if the motor's rotor rotates in one direction when switch 17 is closed and $S_L = 0$, the rotor will rotate in the opposite direction when the switch is open and $S_L = 1$.

The speed of rotation of the rotor is determined mainly by the voltage $V_A$ from voltage source 2, at least when the load on the motor is low. By varying this voltage, as by means of a pedal, it is possible to adapt the speed of the rotor to the work being done, and even to stop it by reducing $V_A$ to zero.

The d.c. voltage issued by source 2 to the stator's windings depends on the opposing torque applied to the motor. When the motor is heavily loaded this current may reach several amperes and saturate the small magnetic circuit of transformer 21 through whose primary it flows. This saturation causes high frequency voltage $V_C$ across the transformer's secondary winding to drop. Self-inductance coil 9, through which the same current flows, serves to compensate this voltage drop. To this end, it comprises a saturable magnetic circuit which causes a decrease in its impedance when the d.c. voltage flowing through it increases. This causes the high frequency current in conductors 5, 5' to increase in dependence on the motor's load, this increase compensating the effects of the saturation of transformer 21 and causing the high frequency voltage across its secondary winding to remain substantially constant.

Clearly, various modifications may be made by the man of the art within the scope of the appended claims to the driving arrangement described above with reference to the drawings.

We claim:

1. An electrical arrangement for driving a rotary tool fitted in a handpiece comprising, external to the handpiece:
   electrical supply means having an output, a source of d.c. voltage, a generator for supplying a high frequency voltage and means for superposing said high frequency voltage on said d.c. voltage and applying the resulting compound voltage to said output;
   two deformable electric conductors, having one end thereof connected to said output; and further comprising, in said handpiece:
   a multi-phase, brushless motor having a magnetized rotor arranged to rotate said tool;
   means connected to the other end of said two conductors to receive said compound voltage and for separating therefrom said d.c. voltage and said high frequency voltage;
   sensor means controlled by said rotor and adapted to generate, during operation, logic signals that are representative of the rotor's angular positions;
   a logic control circuit arranged to generate control signals in response to logic signals generated by the sensor means;
   a drive circuit connected to the motor and arranged to receive said control signals and said d.c. voltage and to issue a multi-phase signal to the motor to cause its rotor to rotate; and
   a rectifying circuit arranged to receive said high frequency voltage and to issue a d.c. voltage to the sensor means, to the logic control circuit and to the drive circuit.

2. An arrangement as in claim 1, wherein said supply means further have means for modulating the high frequency voltage and switch means for controlling the modulation, said switch means having a first operative state for producing a first modulation mode and a second operative state for producing a second modulation mode; said arrangement further comprising, in said handpiece, means for demodulating the high frequency voltage and for generating a logic signal, each level of said logic signal being representative of one of the two modulation modes, and a logic inverting circuit arranged to be supplied with d.c. voltage from the rectifying circuit, to receive the signals generated by the sensor means and the signal representative of the modulation modes, and to issue to the logic control circuit logic signals that are identical to the logic signals from the sensor means in response to one mode of modulation to cause the rotor to rotate in one direction, and logic signals that are opposite to those from the sensor means in response to the other mode of modulation to cause the rotor to rotate in the opposite direction.

3. An arrangement as in claim 2, wherein said high frequency voltage is amplitude modulated by a low frequency voltage.

4. An arrangement as in claim 1, wherein said means for superposing said high frequency voltage on said d.c. voltage include a coupling transformer having a primary winding supplied by said high frequency generator, and a secondary winding having one end connected to one of said two conductors, said d.c. voltage being applied between the other end of the secondary winding and the other conductor; and wherein said means for separating said d.c. voltage from said high frequency voltage include a separation transformer having one end of its primary winding connected to one of said two conductors, and a capacitor having one terminal connected to the other end of said primary winding and its other terminal connected to the second conductor, the high frequency voltage appearing during operation on the secondary winding of the separation transformer and the d.c. voltage appearing on the terminals of the capacitor.

5. An arrangement as in claim 4, wherein a saturatable selfinductance coil is fitted in series in one of said conductors to render the amplitude of the high frequency voltage that appears on the secondary winding of said separation transformer independent of the intensity of the d.c. voltage flowing through said two conductors.

6. An arrangement as in claim 1, wherein said sensor means are photoelectric.

7. An arrangement as in claim 1, wherein said supply means include control means for adjusting said d.c. voltage, the value of said d.c. voltage determining the speed of rotation of said rotor.

8. A handpiece adapted to receive a rotary tool and comprising means for driving said tool, said means including, inside the handpiece:
   a multi-phase, brushless motor having a magnetized rotor arranged to rotate said tool;
   input means for receiving a compound voltage consisting of a high frequency voltage superposed on a d.c. voltage and means for separating said high frequency voltage from said d.c. voltage;
   sensor means controlled by said rotor and adapted to generate, during operation, logic signals that are representative of the rotor's angular positions;
   a logic control circuit arranged to generate control signals in response to logic signals generated by the sensor means;

a drive circuit connected to the motor and arranged to receive said control signals and said d.c. voltage and to issue a multi-phase signal to the motor to cause its rotor to rotate; and a rectifying circuit arranged to receive said high frequency voltage and to issue a d.c. voltage to the sensor means, to the logic control circuit and to the drive circuit 9. A handpiece as in claim 8, wherein the high frequency voltage in the compound voltage received by said input means is modulated in two modes and said tool driving means further include:

means for demodulating the high frequency voltage and for generating a logic signal, each level of said logic signal being representative of one of the two modulation modes; and a logic inverting circuit arranged to be supplied with d.c. voltage from the rectifying circuit, to receive logic signals generated by the sensor means and the logic signal representative of the modulation modes, and to issue to the logic control circuit logic signals that are identical to the logic signals from the sensor means in response to one mode of modulation to cause the rotor to rotate in one direction, and logic signals that are opposite to those from the sensor means in response to the other mode of modulation to cause the rotor to rotate in the opposite direction.

10. A rotary tool drive arrangement for use with a multi-phase brushless motor having a magnetized rotor, comprising: input means for receiving a compact voltage having a high frequency voltage component superposed on a d.c. Voltage and means for separating said high frequency voltage component from said d.c. voltage; motor rotor rotation responsive sensors adapted to generate during the motor operation logic signals that are representative of the rotor's angular position; logic control means for generating control signals in response to logic signals generated by the rotor sensors; drive circuit means connected to the terminals of the motor, for receiving control signals and the d.c. voltage from said separating means, and for issuing a multi-phase signal to the terminals of the motor to cause the motor rotor to rotate; and, rectifying circuit means for receiving the high frequency voltage from said separating means and for outputting a d.c. voltage to the rotor sensors, to the logic control means and to the drive circuit means.

11. A rotary tool drive arrangement according to claim 10, further comprising: electrical supply means for supplying a d.c. voltage and for supplying a high frequency voltage and for superposing the high frequency voltage on the d.c. voltage to produce said compact voltage and supplying the compact voltage to the input means, the supply means including means for modulating the high frequency voltage and switch means for controlling the modulation, the switch means having a first operative state for producing a first modulation mode and a second operative state for producing a second modulation mode.

12. A rotary tool drive arrangement according to claim 11, further comprising: means for demodulating the high frequency voltage and for generating a logic signal, the level of the logic signal being representative of one of the two modulation modes; and, logic inverting circuit means receiving d.c. voltage from the rectifying circuit means, receiving the logic signals generated by the rotor sensors and the signal representative of the modulation modes, the logic inverting circuit means being connected to the logic control means for generating logic signals that are identical to the logic signals from the rotor sensors in response to one mode of modulation to cause the rotor to rotate in one direction, and for generating logic signals that are opposite to those from the rotor sensors in response to the other mode of modulation to cause the rotor to rotate in the opposite direction.

* * * * *